United States Patent [19]

Ohba et al.

[11] Patent Number: 5,359,048
[45] Date of Patent: Oct. 25, 1994

[54] POLYNUCLEOTIDE ENCODING A TOXIN WITH ACTIVITY AGAINST COLEOPTERANS

[75] Inventors: Michio Ohba, Fukuoka; Hidenori Iwahana; Ryoichi Sato, both of Tokyo; Nobukazu Suzuki, Ibaraki; Katsutoshi Ogiwara, Ibaraki; Kazunobu Sakanaka, Ibaraki; Hidetaka Hori, Kanagawa; Shouji Asano; Tadaaki Kawasugi, both of Ibaraki, all of Japan

[73] Assignee: Mycogen Corporation, San Diego, Calif.

[21] Appl. No.: 915,203

[22] Filed: Jul. 23, 1992

[30] Foreign Application Priority Data

Aug. 2, 1991 [JP] Japan .................. 3-193810

[51] Int. Cl.$^5$ ............................ C12N 15/32
[52] U.S. Cl. .................. 536/23.71; 800/205; 435/69.1; 435/252.1; 424/93.461
[58] Field of Search ............. 800/205; 536/23.71; 435/69.1, 252.1, 235.1; 424/93 L

[56] References Cited

U.S. PATENT DOCUMENTS 4,966,765 10/1990 Payne et al. ............... 435/252.5
5,064,648 11/1991 Hickle et al. ............... 424/93 R

FOREIGN PATENT DOCUMENTS 0202739 11/1986 European Pat. Off. .
0337604 10/1989 European Pat. Off. .
0382990  8/1990 European Pat. Off. .
8901515  2/1989 PCT Int'l Appl. .

OTHER PUBLICATIONS

Perlak, et al (Apr. 1991) Proc. Natl. Acad. Sci., USA 88:3324–3328.
Murray, et al (1991) Plant Molecular Biology 16:1035–1050, Abstract.
Couch, T. L. (1980) "Mosquito Pathogenicity of *Bacillus thuringiensis* var. *israelensis*," *Developments in Industrial Microbiology* 22:61–76.
Beegle, C. C. (1978) "Use of Entomogenous Bacteria in Agroecosystems," *Developments in Industrial Microbiology* 20:97–104.
Krieg, V. A., A. M. Huger, G. A. Langenbruch, W. Schnetter (1983) "*Bacillus thuringiensis* var. *tenebrionis*, a new pathotype effective against larvae of Coleoptera," *Z. Ang. Ent.* 96:500–508.
Ohba, M., H. Iwahana, S. Asano, N. Suzuki, R. Sato, and H. Hori (1992) "A unique isolate of *Bacillus thuringiensis* serovar *japonensis* with a high larvicidal activity specific for scarabaeid beetles" *Letters in Applied Microbiology* 14:54–57.
Ohba, Michio, and Keio Aizawa (1986) "*Bacillus thuringiensis* subsp. *japonensis* (Flagellar Serotype 23): A New Subspecies of *Bacillus thuringiensis* with a Novel Flagellar Antigen "Journal of Invertebrate Pathology 48:129–130.

Primary Examiner—Che S. Chereskin
Attorney, Agent, or Firm—Saliwanchik & Saliwanchik

[57] ABSTRACT

*Bacillus thuringiensis* serovar *japonensis* strain Buibui (FERM BP-3465) belonging to *Bacillus thuringiensis* serovar *japonensis* and capable of producing insecticidal toxin proteins to kill coleopterous larvae, and an insecticide containing, as an effective ingredient, the toxin proteins produced are disclosed.

2 Claims, 8 Drawing Sheets

POLYNUCLEOTIDE ENCODING A TOXIN WITH ACTIVITY AGAINST COLEOPTERANS

BACKGROUND OF THE INVENTION

1. Field of the Invention

This invention relates to a novel microorganism belonging to *Bacillus thuringiensis* serovar *japonensis*, to an insecticide derived from this novel microorganism, and to DNA coding for the insecticide.

2. Description of the Related Art

The reported activity spectrum of *B.t.* covers insect species within the order Lepidoptera, many of which are major pests in agriculture and forestry. The activity spectrum also includes the insect order Diptera, which includes mosquitos and black flies. See Couch, T. L. (1980) "Mosquito Pathogenicity of *Bacillus thuringiensis* var. *israelensis*," *Developments in Industrial Microbiology* 22:61–76; Beegle, C. C., (1978) "Use of Entomogenous Bacteria in Agroecosystems," *Developments in Industrial Microbiology* 20:97–104. Krieg et al. (1983) *Z. ang. Ent.* 96:500–508, describe a *B.t.* isolate named *Bacillus thuringiensis* var. *tenebrionis*, which is reportedly active against two beetles in the order Coleoptera. These are the Colorado potato beetle, *Leptinotarsa decemlineata*, and *Agelastica alni.*

In European Patent Application 0 202 739 there is disclosed a novel *B.t.* isolate active against Coleoptera. It is known as *B. thuringiensis* var. *san diego* (*B.t.s.d.*). U.S. Pat. No. 4,966,765 discloses the coleopteran-active *Bacillus thuringiensis* isolate *B.t.* PS86B1. European Patent Application 0 337 604 also discloses a novel *B.t.* isolate active against Coleoptera.

Coleopteran-active *B.t.* strains can be used to control foliar-feeding beetles. The Colorado potato beetle (*Leptinotarsa decemlineata*), for example, is susceptible to the delta-endotoxin of *B.t.s.d.* and larvae are killed upon ingesting a sufficient dose of spore/crystal preparation on treated foliage. Strain cells among *Bacillus thuringiensis* serovar *japonensis* are known to produce insecticidal proteins that kill lepidopteran larvae. However, none of the strain cells among *japonensis* are known to produce toxin proteins other than the insecticidal proteins that kill lepidopterous larvae. Thus, no such strain cells have been available for use as an insecticide to kill insects other than lepidopterans. Furthermore, *Bacillus thuringiensis san diego* and *Bacillus thuringiensis tenebrionis* have no insecticidal effect on larvae of *Anomala cuprea* Hope, which are very destructive to firewood, taro, sweet potato, peanut, and the like.

The current inventors have found a new type of microorganism belonging to *Bacillus thuringiensis* serovar *japonensis* that produces insecticidal proteins to kill coleopterous larvae as distinct from lepidopterous larvae.

BRIEF SUMMARY OF THE INVENTION

The subject invention concerns a novel *Bacillus thuringiensis* (*B.t.*) isolate. The novel *B.t.* isolate, known as *Bacillus thuringiensis* serovar *japonensis* strain Buibui (hereinafter referred to as "*B.t. Buibui*"), has been found to be active against coleopteran pests including the Japanese beetle. A novel δ-endotoxin gene of the invention encodes an ≈130 kDa protein. The nucleotide sequence of this gene is shown in SEQ ID NO. 1. The predicted amino acid sequence of the toxin is shown in SEQ ID NO. 2.

The subject invention also includes variants of *B.t. Buibui* which have substantially the same pesticidal properties as *B.t. Buibui.* These variants would include mutants. Procedures for making mutants are well known in the microbiological art. Ultraviolet light and nitrosoguanidine are used extensively toward this end.

Further, the invention also includes the treatment of substantially intact *B.t.* cells, and recombinant cells containing a gene of the invention, to prolong the pesticidal activity when the substantially intact cells are applied to the environment of a target pest. Such treatment can be by chemical or physical means, or a combination of chemical or physical means, so long as the technique does not deleteriously affect the properties of the pesticide, nor diminish the cellular capability in protecting the pesticide, The treated cell acts as a protective coating for the pesticidal toxin. The toxin becomes available to act as such upon ingestion by a target insect.

BRIEF DESCRIPTION OF THE SEQUENCES

Figure 1:
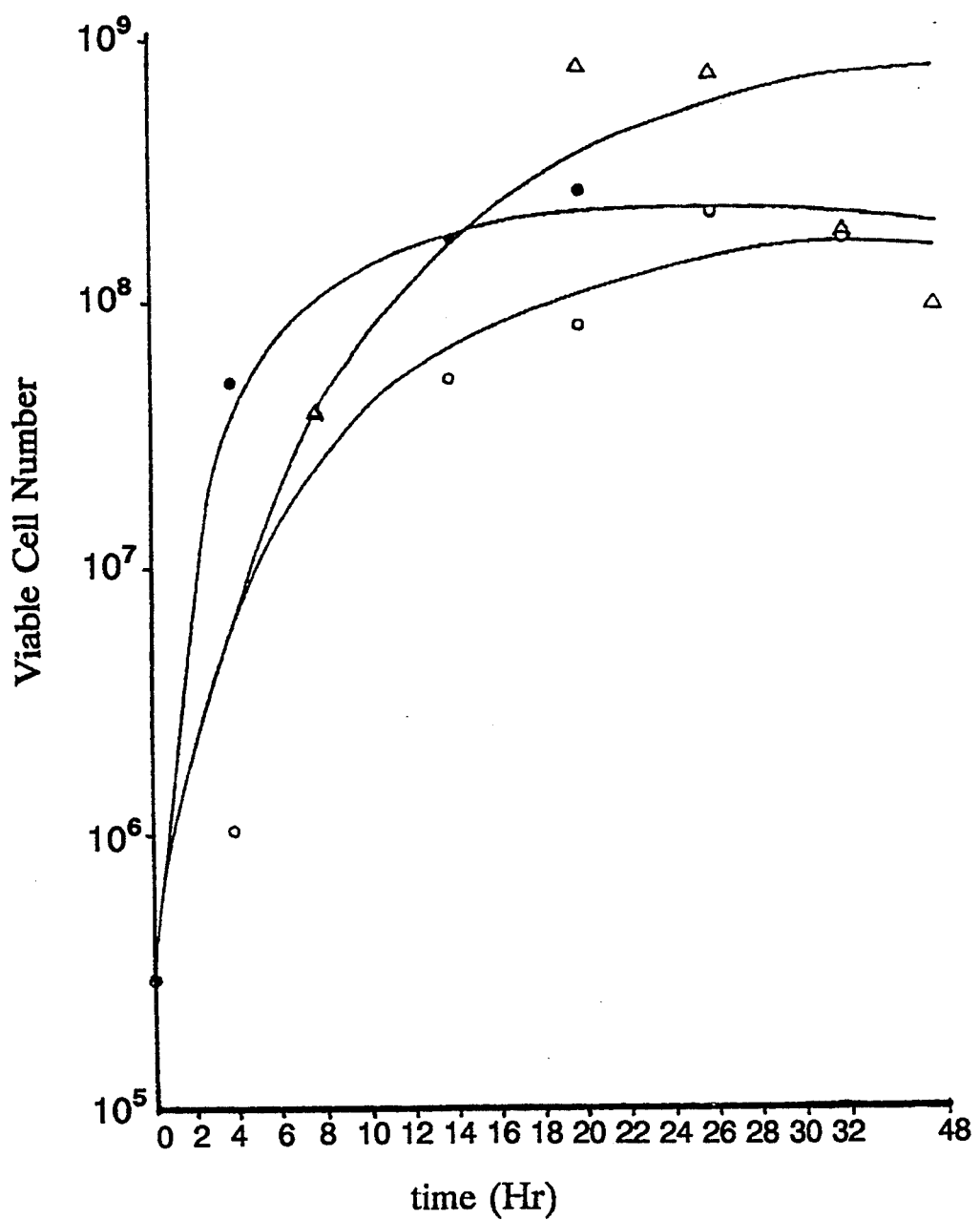
FIG. 1 is a graph showing growth curves of *B.t. Buibui.* The number of colonies produced by splaying the cells in the following agar culture media of the petri dish is measured. —●— LB medium; —○— NB medium; —△— NYS medium.

SEQ ID NO. 1 is the composite nucleotide and amino acid sequence of the novel gene of the invention.

SEQ ID NO. 2 is the predicted amino acid sequence of the toxin.

DETAILED DESCRIPTION OF THE INVENTION

The subject invention pertains to a novel strain of *Bacillus thuringiensis* which has the highly advantageous property of expressing at least one endotoxin which is toxic to coleopterans. The novel microorganism has been designated *Bacillus thuringiensis* serovar *japonensis* strain *Buibui* (hereinafter referred to as "*B.t. Buibui*"). The subject invention further pertains to insecticidal toxin obtainable from *B.t. Buibui* as well as DNA coding for said insecticide. Also disclosed and claimed are microorganisms, other than *Bacillus thuringiensis*, which have been transformed with *B.t. Buibui* DNA so that said transformed microbes express a coleopteran-active toxin. A further aspect of the subject invention is the use of a toxin of the subject invention, or a transformed host-expressing a toxin, to control coleopteran pests. Yet a further aspect of the subject invention pertains to plants transformed with a *B.t. Buibui* DNA coding for toxin active against coleopteran pests.

Novel microorganisms according to the present invention, have been deposited internationally, pursuant to the Treaty of Budapest, with the Fermentation Research Institute, Agency of Industrial Science and Technology, Ministry of International Trade and Industry, which is a recognized international depository organization.

| Culture | Deposit No. | Deposit Date |
| --- | --- | --- |
| *Bacillus thuringiensis* serovar *japonensis* strain Buibui | FERM BP-3465 | June 26, 1992 |
| *Escherichia coli* KBR9207 | FERM BP-3929 | ??? |

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

The invention also includes variants of the subject isolates which variants have genes encoding all or pan of a toxin of the invention. Such microbial variants may be isolated or they can be made by techniques well known to persons skilled in the art. For example, UV irradiation can be used to prepare variants of host organisms. Likewise, such variants may include asporogenous host cells which also can be prepared by procedures well known in the art. For example, an asporogenous mutant can be obtained through ethylmethane sulfonate (EMS) mutagenesis of a novel isolate. A small percentage of the asporogenous mutants will remain intact and not lyse for extended fermentation periods; these strains are designated lysis minus (−). Lysis minus strains can be identified by screening asporogenous mutants in shake flask media and selecting those mutants that are still intact and contain toxin crystals at the end of the fermentation. Lysis minus strains are suitable for a cell fixation process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

The variants can also be made using ultraviolet light and nitrosoguanidine by procedures well known in the art.

Figure 2:
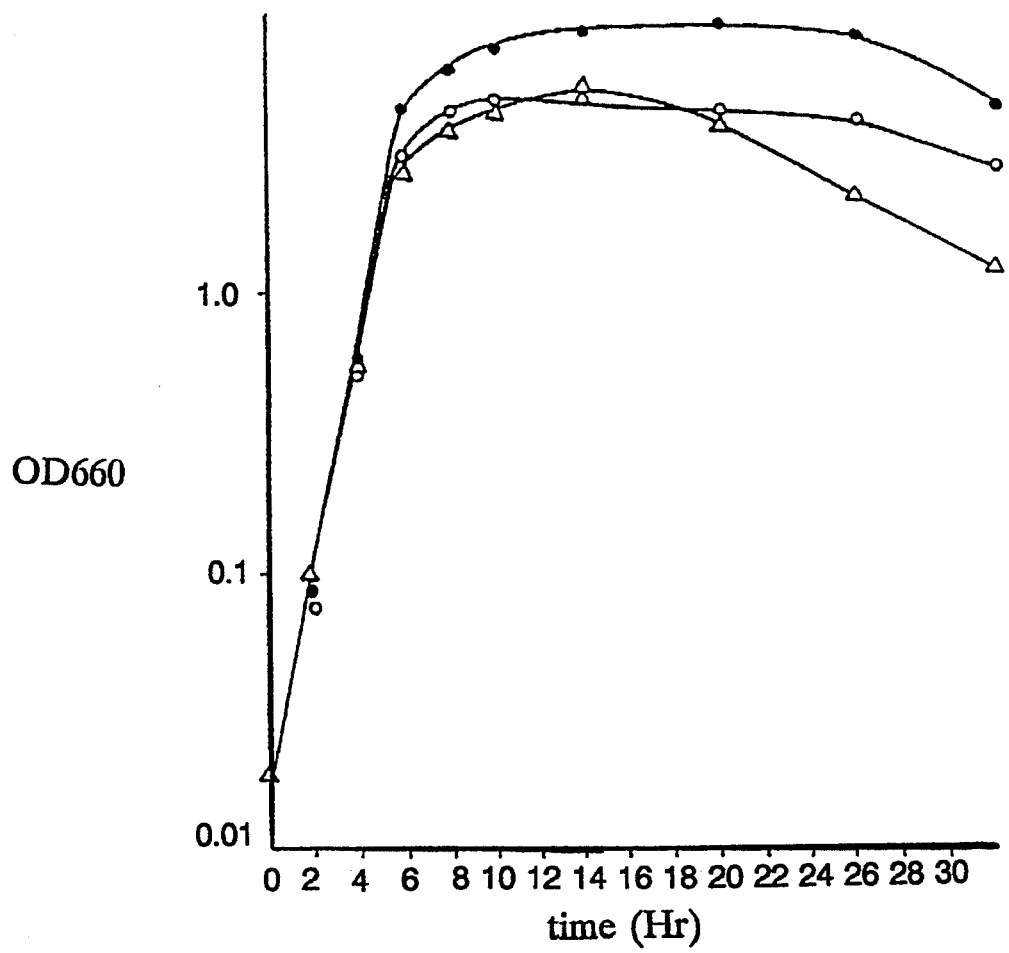
FIG. 2 is a graphs showing growth curves of *B.t. Buibui.* The increase of the number of cells is shown by the absorptive increase of media at 660 nm. —●— LB medium; —○— NB medium; —△— NYS medium.

The novel microorganism, *B.t. Buibui*, specifically exemplified according to the present invention has the following characteristics:

1. Growth in Different Culture Media. This microorganism may be grown and the toxin proteins may be produced in all types of media that can be used for culturing ordinary bacteria. As shown in FIGS. 1 and 2, the microorganism showed ordinary growth patterns in typical culture media such as NYS, L-broth, and bouillon media. That is, the number of cells began to increase logarithmically after lapse of several hours, and the increase stopped upon lapse of 24 hours. Toxins appeared slightly after the increase in the number of cells. The quantity of toxins, when measured in the main band 130 kDa, was 200 to 300 μg/ml medium.

Figure 3:
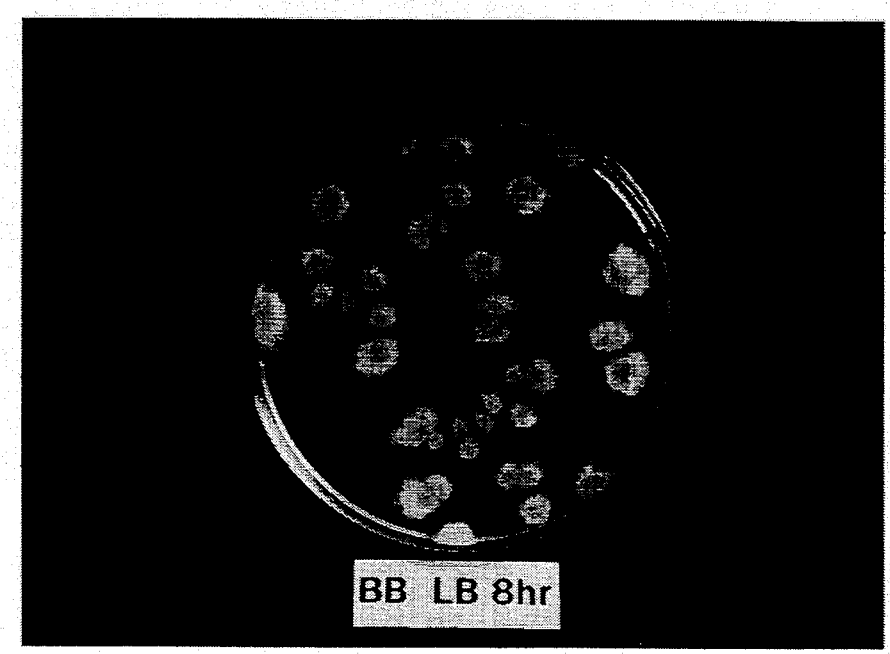
FIG. 3 is a photograph showing colonies of *B.t. Buibui* in LB culture medium. The colonies of *Buibui* strain were cultured in the LB agar culture media for 72 hours after being cultured in the LB culture media for 8 hours.
Figure 4:
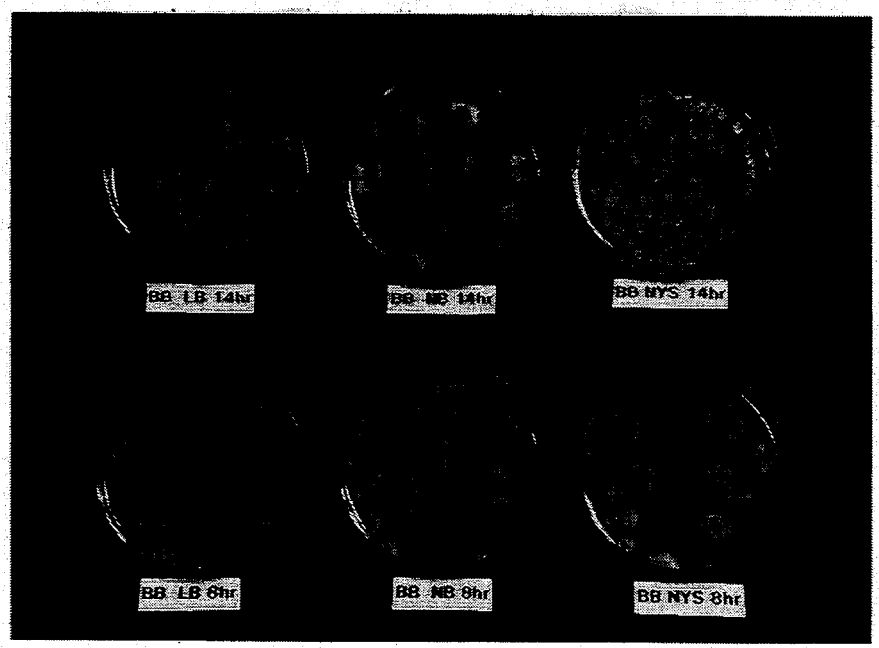
FIG. 4 is a photograph showing colonies of *B.t. Buibui* in various culture media. The colonies of Buibui strain were cultured in the respective agar culture media for 72 hours after being cultured in the LB, NB, and NYS culture media for 8 hours and 14 hours.
Figure 5:
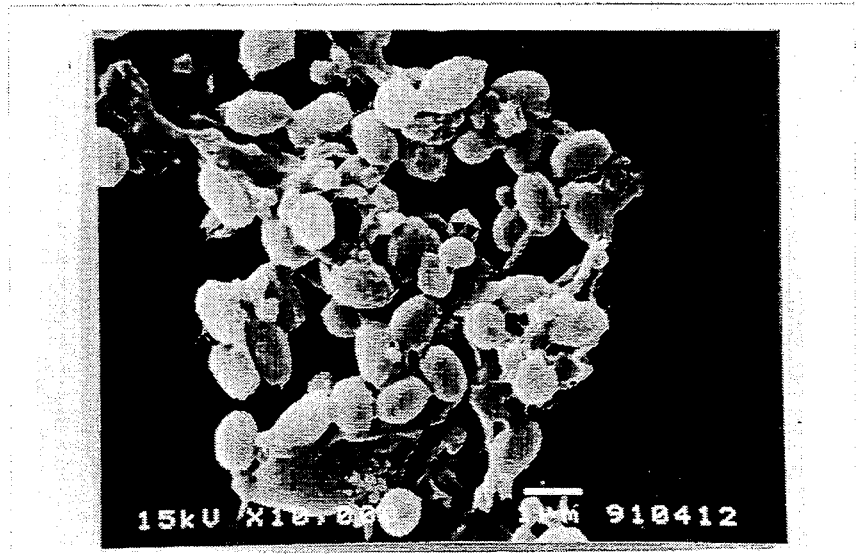
FIG. 5 is a photograph of *japonensis* strain taken with a scanning electron microscope. The dark arrows show crystals of toxin proteins. The elliptic members having wrinkled surfaces are spores.
Figure 6:
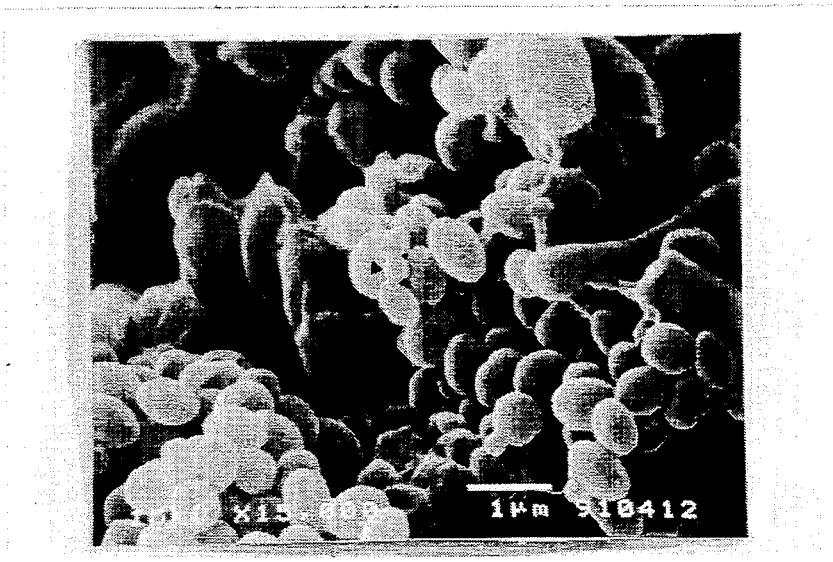
FIG. 6 is a photograph of *B.t. Buibui* taken with the scanning electron microscope. The dark arrows show crystals of toxin proteins. The elliptic members having wrinkled surfaces are spores.
Figure 7:
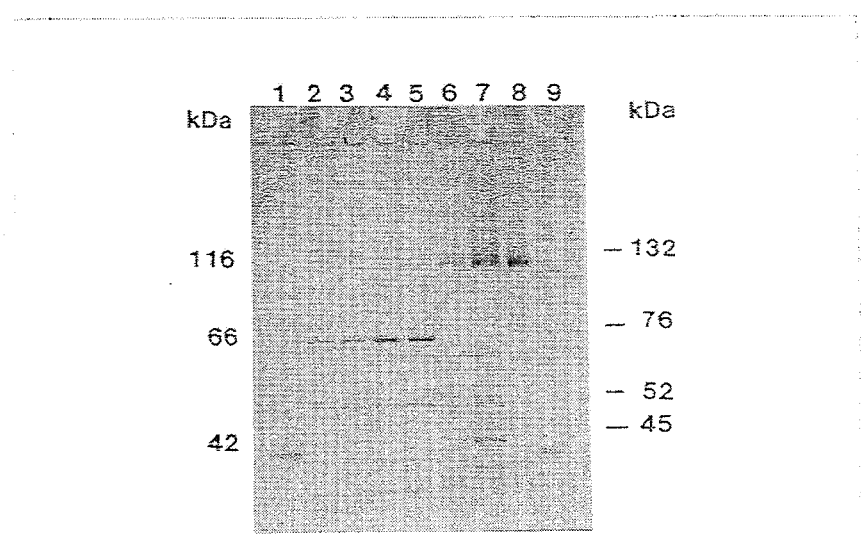
FIG. 7 is a photograph showing sodium dodecyl sulfate polyacrylamide gel electrophoresis. Lane 1 is a molar weight marker. Lane 2 shows toxin proteins produced by *japonensis* strain (5 μl). Lane 3 shows toxin proteins produced by *japonensis* strain (10 μl). Lane 4 shows toxin proteins produced by *japonensis* strain (15 μl). Lane 5 shows toxin proteins produced by *japonensis* strain (20 μl). Lane 6 shows toxin proteins produced by *Buibui* strain (5 μl). Lane 7 shows toxin proteins produced by *Buibui* strain (10 μl). Lane 8 shows toxin proteins produced by *Buibui* strain (5 μl). Lane 9 is a molar weight marker.

2. Morphological Characteristics. As shown in FIGS. 3 and 4, the colonies produced have surface gloss on an agar medium, and spread thinly over the agar surfaces without swelling. Peripheral roughs show characteristics of ordinary Bacillus cells. The color of the colonies is light beige.

When observed through a scanning electron microscope, both *Bacillus thuringiensis* serovar *japonensis* and *Bacillus thuringiensis* serovar *japonensis* strain *Buibui* show spherical crystal proteins. These are distinct from the bipyramid crystals commonly observed with other *B.t.* cells lethal to lepidopterous larvae.

3. Biochemical Appearance. The following tests have been conducted to evaluate the biochemical characteristics of *B.t. Buibui* as compared with conventional *japonensis* strains:

Test 1. Serotyping using antibodies produced against flagellar antigens: This is a method for identifying an unknown organism by employing an antibody active to the proteins of flagella of Bacillus organisms, and utilizing an antigen-antibody reaction in which the flagellar proteins of the unknown organism act as the antigens. Japonensis strain is a subspecies classified and recognized as H23 type (*J. Invertebr. Pathol.* 32:303–309, 1978; *J. Invertebr. Pathol.* 48:129–130, 1986). *B.t. Buibui* is reactive with H-antigen of japonensis strain. This property is serologically equivalent to that of*japonensis* strain. Thus, taxonomically, *B.t. Buibui* belongs to the same subspecies as *japonensis* strain. Details of this test are as follows:

(1) Preparation of flagellar H-serum: Forty known types or H-antigen standard strains of *Bacillus thuringiensis* were used. Microorganisms having excellent mobility were selected by using a Craigie tube (0.5% semifluid agar medium), and formalin-killed organisms were prepared. Rabbits were immunized with these organisms. H-serum was prepared by absorbing, from respective antisera, antibodies reactive to *Bacillus thuringiensis* cell antigens. The cell antigens were prepared by heating them to 100° C. and separating the flagella.

(2) Identification of H-antigen: Serum types of H-antigen were identified through agglutination reactions on slide glass (Ohba and Aizawa [1978]*J. Invertebr. Pathol.* 32:303–309). Agglutination values of H-serum were measured through in vitro agglutination reactions (Ohba and Aizawa, supra).

(3) Results: Japonensis strain was particularly agglutinated only by the serum for standard strain cells of serovar *japonensis* (H-antigen 23) among standard sera including 40 known types of flagellar antigens only. The agglutination value of *japonensis* H-serum for corresponding homo-antigens was 12,800-fold, and the agglutination value thereof for *Buibui* strain was 6,400-fold. The agglutination value of *B.t. Buibui* H-serum for homo was 12,800-fold and the agglutination value thereof for *japonensis* standard strain was 6,400-fold. Thus, the two strain cells are determined to be the same species.

Test 2. Insecticidal spectral of crystal proteins produced by *japonensis* strain and *B.t. Buibui:* As shown in Table 1, the insecticidal proteins produced by *B.t. Buibui* showed an insecticidal effect in a concentration of 0.125 to 12.5 μg/ml on *Anomala cuprea* Hope, a coleopteran. However, the insecticidal proteins produced by the *japonensis* strain did not show an insecticidal effect even in a concentration of 100 μ/ml. As shown in Table 2, the insecticidal proteins produced by *japonensis* strain showed a high degree of activity with respect to larvae of lepidopterans such as *Plutella xylostella,* Adoxophyes sp., and *Bombyx mori.* However, the insecticidal proteins produced by *B.t. Buibui* showed little or a very low degree of activity. These results demonstrate that the two strains cannot be said to be the same strains. Furthermore, the observance of coleopteran activity, but no lepidopteran activity is quite surprising and unexpected.

TABLE 1

Insecticidal effects of *japonensis* strain and *B.t. Buibui* on *Anomala cuprea* Hope

| Toxin dosage | Death rates* (%) | | |
|---|---|---|---|
| (μg 130 kDa protein/ml) | 7th day | 14th day | 22nd day |
| *B.t. Buibui* cells | | | |
| 12.5 | 65 | 95 | 95 |
| 1.25 | 45 | 95 | 100 |
| 0.125 | 0 | 30 | 80 |
| Japonensis strain cells | | | |
| 100 | 0 | 0 | 0 |

*Number of samples = 20 larvae in the first instar.

TABLE 2

Insecticidal activities of *japonensis* strain and Buibui strain with respect to some lepidopterans.

| Samples | Toxin dosage (μg 130 kDa protein/ml) | Death rates* (%) Buibui | *japonensis* |
|---|---|---|---|
| *Plutella xylostella* | 50 | 0 | 100 |
| *Spodoptera litura* | 500 | 0 | — |
| | 50 | 0 | 4 |
| Adoxophyes sp. | 50 | 6 | 47 |
| *Spodoptera exigua* | 50 | 10 | 3 |
| *Bombyx mori* | 50 | 0 | 70 |

*Number of samples = 50 larvae in the first to third instar.

Test 3. Electrophoresis of insecticidal proteins accumulating in the cells of *japonensis* strain and *B.t. Buibui: B.t. Buibui* produces, in the cells, spherical crystalline proteins as does *japonensis* strain (FIGS. 5 and 6). The crystalline proteins were isolated from the culture medium by a standard method (Goodman, N. S., R. J. Gottfried, M. J. Rogoff [1987] *J. Bacteriol.* 34:485). After purification, the proteins were dissolved in a 0.4N alkali solution, and analyzed through sodium dodecyl sulfate polyacrylamide gel electrophoresis (SDS-PAGE). As shown in FIG. 7, *japonensis* strain has a main band at about 76 kDa, and a different band at 52 kDa. *B.t. Buibui* has a main band at about 130 kDa, and different bands at 52 kDa and 45 kDa. These electrophoresis patterns clearly show that the two types of crystalline proteins have different ingredients.

Test 4. Difference in adoptivity in culture media between *japonensis* strain and *B.t. Buibui*: As shown in Table 3, *japonensis* strain adopts glucose, salicin, and maltose, does not adopt mannose, and adopts cellobiose to a certain degree. *B.t. Buibui* can adopt all of these substances.

These features show that, taxonomically, *B.t. Buibui* is classified by serotype as *Japonensis* strain, but clearly is a cell different from *japonensis* strain.

TABLE 3

| Sugars | *japonensis* | Buibui |
|---|---|---|
| glucose | ++ | ++ |
| D-(+)-xylose | − | − |
| D-(+)-arabinose | − | − |
| mannitol | − | − |
| galactose | − | − |
| mannose | − | ++ |
| salicin | ++ | ++ |
| sucrose | +− | +− |
| D-(+)-cellobiose | +− | ++ |
| maltose | ++ | ++ |
| lactose | − | − |
| acetoin | + | + |

TABLE 3-continued

| Sugars | japonensis | Buibui |
|---|---|---|
| urease | + + | + + |

+ + + = adopt very well; + = adopt well, + − = adopt; − = do not adopt

*B.t. Buibui* can be cultured using standard art media and fermentation techniques. Specific examples of fermentation media and techniques are provided in the examples which follow. Upon completion of the fermentation cycle, the bacteria can be harvested by first separating the *B.t.* spores and crystals from the fermentation broth by means well known in the art. The recovered *B.t.* spores and crystals can be formulated into a wettable powder, liquid concentrate, granules, or other formulations by the addition of surfactants, dispersants, inert carriers and other components to facilitate handling and application for particular target pests. These formulation and application procedures are all well known in the art.

DNA containing the toxin gene from *B.t. Buibui* can be purified from *E. coli* KBR9207 by standard procedures well known in the art. The toxin gene can be excised from the plasmid DNA by restriction enzyme digestion. This subject invention pertains not only to the specific DNA sequence shown in SEQ ID NO. 1, but also to variations of this sequence which code for an amino acid sequence having activity against coleopteran characteristics of the toxin produced by *B.t. Buibui.* These DNA sequences would be expected to have a high degree of homology and, for example, would be expected to hybridize with each other and/or common probes or primers under high stringency conditions. Similarly, the subject invention pertains not only to the protein having the amino acid sequence shown in SEQ ID NO. 2, but also to equivalent toxins having the same or similar biological activity of the toxin shown in SEQ ID NO. 2. These equivalent toxins may have amino acid homology with the toxin disclosed and claimed herein. This amino acid homology will typically be greater than 50%, preferably be greater than 75%, and most preferably be greater than 90%. The amino acid homology will be highest in certain critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table provides a listing of examples of amino acids belonging to each class.

TABLE 4

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

The genes and toxins according to the subject invention include not only the full length sequences disclosed herein but also fragments of these sequences, or fusion proteins, which retain the characteristic coleopteran activity of the toxins specifically exemplified herein.

It should be apparent to a person skilled in this art that genes coding for coleopteran-active toxins can be identified and obtained through several means. The specific genes may be obtained from a culture depository as disclosed herein. Alternatively, these genes, or portions thereof, may be constructed synthetically, for example, by use of a gene machine. Variations of these genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which code for active fragments may be obtained using a variety of other restriction enzymes. Proteases may be used to directly obtain active fragments of these toxins.

DNA of the subject invention, which codes for coleopteran-active toxin, can be introduced into a wide variety of microbial and plant hosts. Expression of the DNA results, directly or indirectly, in the production and maintenance of the pesticide. With suitable hosts, e.g., Pseudomonas, the microbes can be applied to the situs of coleopteran insects where they will proliferate and be ingested by the insects. The result is a control of the unwanted insects. Alternatively, a microbe hosting the toxin-coding DNA can be treated under conditions that prolong the activity of the toxin produced in the cell. The treated cell then can be applied to the environment of target pest(s). The resulting product retains the toxicity of the *B.t.* toxin.

Where the *B.t.* toxin-coding DNA is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina. R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing the *B.t.* DNA expressing the toxin into the microorganism host under conditions which allow for stable maintenance and expression of the gene. These methods are well known and easily practiced by those skilled in this art. The transformants can be isolated in accordance with conventional ways, usually employing a selection technique, which allows for selection of the desired organism as against unmodified organisms or transferring organisms, when present. The transformants then can be tested for pesticidal activity.

The *B.t.* cells can be treated prior to formulation to prolong the pesticidal activity when the cells are applied to the environment of a target pest. Such treatment can be by chemical or physical means, or by a combination of chemical and/or physical means, so long as the technique does not deleteriously affect the properties of the pesticide, nor diminish the cellular capability in protecting the pesticide. Examples of chemical reagents are halogenating agents, particularly halogens of atomic no. 17-80. More particularly, iodine can be used under Mild conditions and for sufficient time to achieve the desired results. Other suitable techniques include treatment with aldehydes, such as formaldehyde and glutaraldehyde; anti-infectives, such as zephiran chloride; alcohols, such as isopropyl and ethanol; various histologic fixatives, such as Bouin's fixative and Helly's fixative (See: Humason, Gretchen. L., *Animal Tissue Techniques,* W. H. Freeman and Company, 1967); or a combination of physical (heat) and chemical agents that prolong the activity of the toxin produced in the cell when the cell is applied to the environment of the target pest(s). Examples of physical means are short wavelength radiation such as gamma-radiation and X-radiation, freezing, UV irradiation, lyophilization, and the like. The cell will usually be intact and be substantially in the proliferative form when treated, rather than in a spore form, although in some instances spores may be employed.

The treated cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the *B.t.* insecticidal gene may be grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* or transformed cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include theological agents, surfactants, emulsifiers, dispersants, or polymers.

Another approach that can be taken is to incorporate the spores and crystals of *B.t. Buibui* into bait granules containing an attractant and applying these granules to the soil for control of soil-inhabiting Coleoptera. Formulated *B.t. Buibui* can also be applied as a seed-coating or root treatment or total plant treatment.

The pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the coleopteran pest(s), e.g., plants, soil or water, by spraying, dusting, sprinkling, or the like.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing *B.t. Buibui*

A subculture of *B.t. Buibui* can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |
| pH 7.2 | |

The salts solution and $CaCl_2$, solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and crystals, obtained in the above fermentation, can be isolated by procedures well known in the art. A frequently-used procedure is to subject the harvested fermentation broth to separation techniques, e.g., centrifugation.

EXAMPLE 2

Further Methods for Culturing B.t. Buibui

B.t. Buibui easily grows in culture media commonly used for culturing bacteria, such as L-broth, nutrient broth, and the like, and produces spores and crystalline proteins. Inventors have reviewed highly productive media for culturing B.t. Buibui to produce insecticidal ingredients including the crystalline proteins.

First, $3.3 \times 10^5$ spores were inoculated into an agar medium on a 9 cm petri dish. The crystalline proteins produced in 10 days were observed through a microscope. A medium having $MnSO_4$ (10-#M) added to L-broth was the most productive, the order of productivity being as follows:

L-broth+$MnSO_4$>spizizen+amino acid>L-broth>PGSM>spizizen+casamino acid+vitamin>s-pizizen+casamino acid>NYS>NYS+casamino acid.

The respective media have the following compositions:

L-broth: 10 g of tryptose, 5 g of yeast extract, and 5 g of table salt, all per 1 liter, and pH=7.18 to 7.2.

Spizizen: 14 g of potassium I-hydrogen phosphate ($K_2H$), 6 g of potassium 2-hydrogen phosphate ($KH_2PO_4$), 2 g of ammonium sulfate, 0.2 g of magnesium sulfate, 1 g of sodium citrate, and 5 g of glucose, all per 1 liter, and pH=7.0.

NYS: 1.25 g of nutrient broth, 1.25 g of trypton, 0.5 g of yeast extract, 10.3 g of calcium chloride, 20.35 g of magnesium chloride, 1.0 g of manganese chloride, 0.02 g of iron sulfate, and 0.02 g of zinc sulfate, all per 1 liter, and pH=7.2.

NYS+casamino acid: 2.0 g of casamino acid added to the above NYS medium, and pH=7.2.

Next, in preparing an insecticide using the insecticidal crystalline proteins produced by the subject cells and effective on coleopterous larvae, the microorganisms according to the invention are cultured in the various media noted above, or in solid media such as fish meal, soy bean powder and the like, or in wastes from starch or sugar processing such as corn syrup and corn steep. The cells cultured by the various methods as above are condensed into creamy form. This is appropriately diluted with water or the like to be sprayed as an insecticide. An antiseptic, extender, and the like, may be mixed into the creamy substance by a usual method. The creamy substance may subsequently be reduced to powder form by means of a spray dryer.

The above method uses the cells themselves which produce the toxin proteins. However, only the crystalline proteins may be used after culturing the cells until autolysis. The product thus obtained is used as a viable microbe cell preparation since the cells produce spores. The toxin proteins produced by these cells do not show toxicity to Bombyx mori. Thus, use of the viable microbe cell preparation having spores is not destructive at all to silk culture. Further, the spores may be killed with a suitable compound for use as a killed microbe cell preparation.

A method of spraying the above preparation will be described next. Coleopterous larva to be killed usually live in soil. Thus, the insecticide having the subject cells as an effective ingredient may be sprayed into soil, or may be scattered together with leaf mold which is immediately followed by a mixing operation with a cultivator or the like. A suspension of the above insecticide may be injected directly into soil by using an automatic or manual injector or the like. For this purpose, a fully automatic injector may be installed on a cultivator.

EXAMPLE 3

Insecticidal Activity of B.t. Buibui with Respect to Anomala cuprea Hope, a Coleopteran As noted hereinabove, Buibui strain shows a very high degree of insecticidal activity not reported heretofore, with respect to Anomala cuprea Hope. The insecticidal activity of B.t. Buibui was examined using larvae of Anomala cuprea Hope in the first to third instars.

The activity was evaluated as follows: 2 ml of water containing insecticidal ingredients was added to 2 g of dry leaf mold. The mixture was placed in a plastic cup. The larvae were then placed one after another and kept therein for a predetermined time.

The insecticidal ingredients included a culture solution of Buibui strain (i.e., a solution containing Buibui strain cells) and crystalline toxin proteins isolated from the culture solution and purified. The insecticidal activity of each ingredient was examined. It is to be noted that the death rate is the number of dead larvae divided by the total number of larvae.

Figure 8:
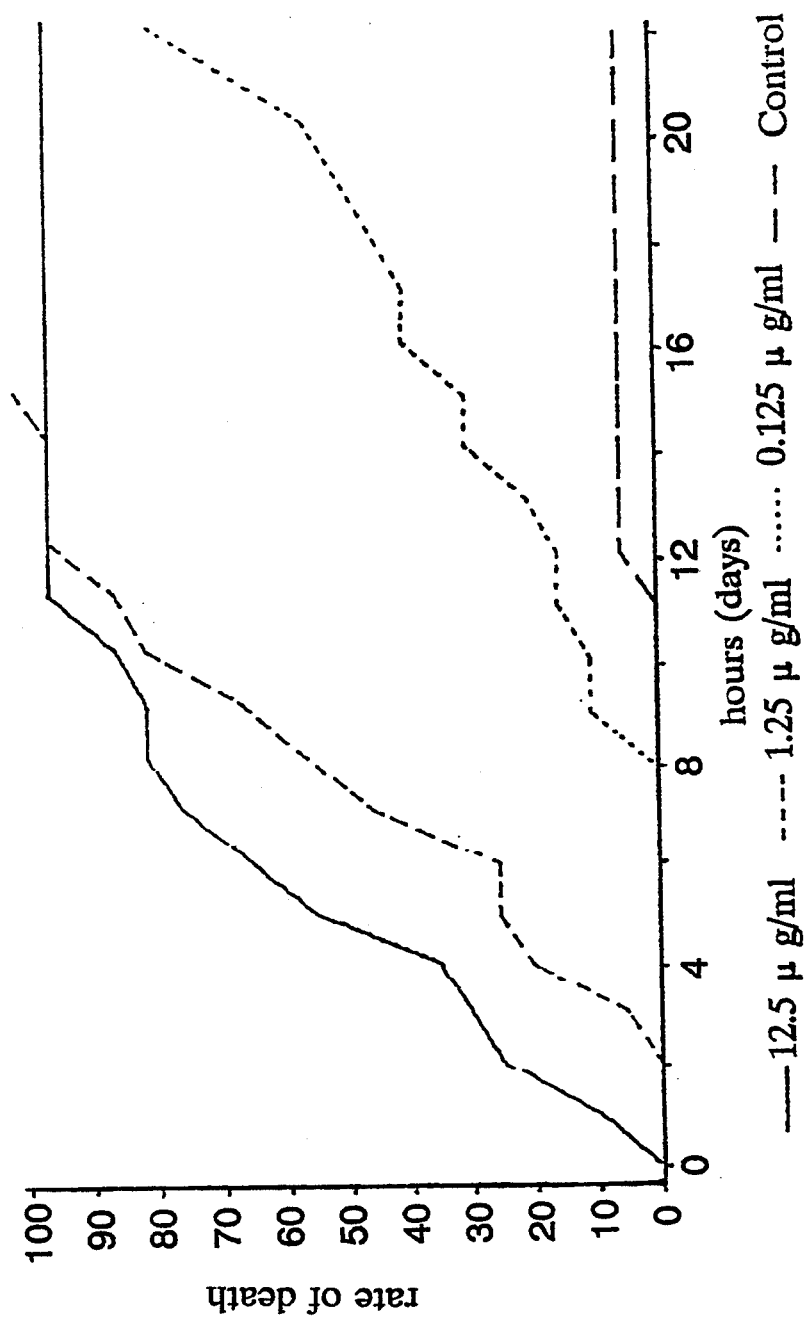
FIG. 8 is a graph showing time-dependent death curves of larvae of *Anomala cuprea* Hope.—12.5 μg/ml;—1.25 μg/ml;—0.125 μg/ml;—control.

FIG. 8 shows how the death rate varies with lapse of time depending on quantity of the insecticidal ingredient (toxin) comprising the culture solution. It will bee seen that 100% death rate is obtained with a low toxin dosage of 0.125 µg/ml and with a high dosage of 12.5 µg/ml. It has been found, however, that twice the time is taken before all the larvae were killed in the case of a low concentration.

The term "control" in FIG. 8 signifies variations occurring when only water containing no toxin is applied.

As shown in Table 5, the insecticidal ingredient comprising the crystalline proteins isolated and purified, showed insecticidal activity on its own. No insecticidal activity was detected with crystals 0.1 µg/ml. However, 100% death rate was obtained, though slowly, when the culture solution containing 130 kDa proteins in 1 µg/ml was applied to Anomala cuprea Hope as noted hereinabove (FIG. 8). This is considered due to the fact that spores present in the cells cooperate with the crystalline proteins in Anomala cuprea Hope to show the high degree of activity, and not that activity is lost due to denaturation of the proteins in the course of purification of the crystalline proteins. Thus, the insecticide may contain the cells.

TABLE 5

Insecticidal activities of culture solution and crystalline proteins of Buibui strain with respect to Anomala cuprea Hope

| Toxin dosage (µg 130 kDa protein/ml) | Death rates* (%) | | |
|---|---|---|---|
| | 7th day | 14th day | 21st day |
| Culture solution | | | |
| 10 | 60 | 100 | |
| 1 | 40 | 95 | 100 |
| Crystalline proteins | | | |
| 10 | 50 | 100 | |
| 1 | 0 | 10 | 20 |

TABLE 5-continued

Insecticidal activities of culture solution and crystalline proteins of Buibui strain with respect to *Anomala cuprea* Hope

| Toxin dosage (μg 130 kDa protein/ml) | Death rates* (%) | | |
|---|---|---|---|
| | 7th day | 14th day | 21st day |
| 0.1 | 0 | 0 | 0 |

*Number of samples = 20 larvae in the first instar. The cells were cultured in NYS.

EXAMPLE 4

Insecticidal Effects of *B.t. Buibui* on Larvae of Other Coleopterans

As shown in Table 6, Buibui strain showed a higher degree of insecticidal activity with respect also to *Anomala rufocuprea* Motschulsky, *Anomala schoenfeldti* Ohaus, apart from *Anomala cuprea* Hope. Thus, Buibui strain is expected to show insecticidal effect on larvae of several other *Minela splendens*. Thus, the insecticide is not limited in application to these three types of coleopterans.

TABLE 6

Insecticidal activities of crystalline proteins produced by Buibui strain with respect to *Anomala rufocuprea* Motschulsky and *Anomala schoenfeldti* Ohaus

| Insects | Toxin dosage (μg 130 kDa protein/ml) | Death rates | | | | | |
|---|---|---|---|---|---|---|---|
| | | 4 | 7 | 10 | 14 | 18 | 21st days |
| *Anomala schoenfeldti* Ohaus | 50 | 0 | 10 | 20 | 30 | 60 | 90 |
| *Anomala rufocuprea* Motschulsky | 50 | 0 | 10 | 20 | 30 | 60 | 100 |
| Larvae in 3rd instar of *Anomala rufocuprea* Motschulsky | 50 | 0 | 10 | 30 | 30 | 70 | 90 |
| Control | 0 | 0 | 0 | 0 | 0 | 0 | 10 |

The insects other than the larvae in the third instar of *Anomala rufocuprea* Motschulsky were all larvae in the first instar. The crystals were purified from cells cultured in NYS. The number of samples was 10.

The term "control" above shows results obtained when only water containing no toxin is applied (in a comparative test).

EXAMPLE 5

Insecticidal Effects on Other Coleopterans

The insecticidal activity of Buibui strain was examined, using larvae in the first instar of *Anomala albopilosa*, larvae in the first instar of *Anomala daimiana*, larvae in the first instar of *Minela splendens*, larvae in the first instar of *Popillia japonica*, and larvae in the second instar of *Blitopertha orientalis*. The samples were young larvae hatched from eggs of adults collected outdoors and temporarily bred in a commercially available leaf mold.

The testing method was as follows: 1 gram of leaf mold dried and sterilized in a dry oven at 160° C. for 60 minutes was weighed with a cup having a lid and a capacity of about 30 ml. Buibui culture in a predetermined concentration was mixed into the cup and sufficiently stirred, and then one larva was placed therein. A plurality of such mixtures were prepared, and bred in a thermostatic chamber at 25° C. The death rate was checked on the 7th, 14th, and 21st days to determine potency of *Buibui*. The results are shown in Table 7.

TABLE 7

| Larvae | Toxin dosage 130 kDa protein μg/g leaf mold | Death rates (%) | | |
|---|---|---|---|---|
| | | 7th | 14th | 21st day |
| *Anomala albopilosa* in first instar | 50 | 100 | 100 | 100 |
| | 0.1 | 0 | 0 | 0 |
| *Anomala daimiana* in first instar | 50 | 0 | 50 | 70 |
| | 0.1 | 25 | 25 | 25 |
| *Minela splendens* in first instar | 50 | 100 | 100 | 100 |
| | 0.1 | 0 | 100 | 100 |
| *Popillis japonica* in first instar | 50 | 100 | 100 | 100 |
| *Blitopertha orientalis* in second instar | 50 | 100 | 100 | 100 |

The number of samples were 8 and 5 for *Anomala daimiana* and *Blitopertha orientalis*, respectively, and 10 for all the others.

As noted above, Buibui strain showed insecticidal activity with respect to *Anomala albopilosa, Anomala daimiana, Minela splendens, Popillia japonica,* and *Blitopertha orientalis*. In the case of *Anomala daimiana*, the death rate was 70% after 21 days, which is lower than the rates of the other insects. However, no increase in the weight was observed, and it was obvious that the larvae of *Anomala daimiana* were to die in due course. Thus, although some delays were observed, the cessation of food intake is considered equivalent to death. Particularly important is the insecticidal property to kill what are known as Japanese beetles, which are causing a serious problem in the United States.

Having determined the activity with respect to several coleopterans, the fact that the activity with respect to Popillia, Minela, and Blitopertha species as well as Anomala species suggests that the subject cells are not limited in application to those insects listed in Tables 6 and 7 but are applicable to a wide variety of coleopteran pests.

EXAMPLE 6

Activity of Beta-Exotoxin

Some of Bacillus strain cells excrete into culture media beta-exotoxin, which is a nucleotide derivative. It has an insecticidal effect similar to that of toxin proteins. Beta-exotoxin shows teratogenic action with respect to larvae of house flies, which provides a basis for evaluating the activity of beta-exotoxin. However, as shown in Table 8, when a supernatant of culture was prepared from a medium of *Buibui* strain by a usual method and applied to house flies, Buibui strain showed no teratogenesis with their pupation rate and eclosion rate remaining unaffected. When the above treating medium of Buibui strain was applied to *Anomala cuprea* Hope, its larvae remained alive after lapse of 14 days as shown in Table 9. The results of this test show that the insecticidal effect of Buibui strain on *Anomala cuprea* Hope does not depend on beta-exotoxin.

That is, beta-exotoxin does not exist to the extent of influencing the test results.

TABLE 8

Effect of beta-exotoxin in Buibui strain culture medium on house flies

| | pupation rate (%) | eclosion rate (%) |
|---|---|---|
| Buibui culture | 86.7 | 80 |
| Standard betaexotoxin | | |

TABLE 8-continued

Effect of beta-exotoxin in Buibui strain culture medium on house flies

|  | pupation rate (%) | eclosion rate (%) |
|---|---|---|
| 2 ppm | 90 | 0 |
| 0.2 ppm | 100 | 0 |
| Distilled water | 93.3 | 93.3 |

TABLE 9

Insecticidal effect of Buibui strain culture medium* on *Anomala cuprea* Hope

|  | Death rates (%) | |
|---|---|---|
|  | 7th day | 14th day |
| Buibui culture* | 0 | 0 |
| Distilled water | 0 | 0 |

*The above Buibui medium refers to the medium remaining after strain cells are removed from the medium by centrifugal separation.

EXAMPLE 7

Insertion of Toxin Gene Into Plants

One aspect of the subject invention is the transformation of plants with genes coding for a coleopteran-active toxin. The transformed plants are resistant to attack by coleopterans.

Genes coding for coleopteran-active toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence coding for the *B.t.* toxin can be inserted into the vector at a suitable restriction site. The resulting plasmid is used for transformation into *E. coli.* The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (51985) In: *The Binary Plant Vector System,* Offset-durkkerij Kanters B. V., Alblasserdam, Chapter 5; Fraley et al., *Crit. Rev. Plant Sci.* 4:1–46; and An et al. (1985) *EMBO J.* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into, a plant host cell. Those techniques include transformation with T-DNA using *Agrobacterium tumefaciens* or *Agrobacterium rhizogenes* as transformation agent, fusion, injection, or electroporation as well as other possible methods. If agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in agrobacteria. The intermediate vector can be transferred into *Agrobacterium tumefaciens* by means of a helper plasmid (conjugation). Binary vectors can replicate themselves both in *E. coli* and in agrobacteria. They comprise a selection marker gene and a linker or polylinker which are framed by the right and left T-DNA border regions. They can be transformed directly into agrobacteria (Holsters et al. [1978] *Mol. Gen. Genet.* 63:181–187). The agrobacterium used as host cell is to comprise plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

EXAMPLE 8

Cloning of Novel *B. thuringiensis* Genes Into Insect Viruses

A number of viruses are known to infect insects. These viruses include, far example, baculoviruses and entomopoxviruses. In one embodiment of the subject invention, ant-active genes, as described herein, can be placed with the genome of the insect virus, thus enhancing the pathogenicity of the virus. Methods for constructing insect viruses which comprise *B.t.* toxin genes are well known and readily practiced by those skilled in the art. These procedures are described, for example, in Merryweather et al. (Merryweather, A. T., U. Weyer, M. P. G. Harris, M. Hirst, T. Booth, R. D. Possee (1990) *J. Gen. Virol.* 71:1535–1544) and Martens et al. (Martens, J. W. M., G. Honee, D. Zuidema, J. W. M. van Lent, B. Visser, J. M. Vlak (1990), *Appl. Environmental Microbiol.* 56(9):2764–2770).

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. An isolated polynucleotide molecule encoding a toxin having activity against coleopterans wherein said toxin has the amino acid sequence in SEQ ID NO. 2.

2. The isolated polynucleotide molecule, according to claim 2, comprising DNA encoding a toxin active against coleopterans wherein said DNA has the nucleotide sequence of SEQ ID NO. 1.

* * * * *

UNITED STATES PATENT AND TRADEMARK OFFICE
CERTIFICATE OF CORRECTION

PATENT NO. : 5,359,048
DATED : October 25, 1994
INVENTOR(S) : Michio Ohba, et. al.

It is certified that error appears in the above-indentified patent and that said Letters Patent is hereby corrected as shown below:

Column 30, line 62: Delete "claim 2" insert --claim 1--
Column 2, line 27: Delete "is a graphs" insert ---is a graph--
Column 2, line 62: Delete ""—1.25 $\mu$/ml; — 0.125 $\mu$g/ml; — control." insert------1.25 $\mu$g/ml;·····0.125 $\mu$g/ml;— — control.--
Column 3, line 65: Delete "all or pan" insert --all or part--
Column 5, line 58: Delete "$\mu$/ml" insert --$\mu$g/ml--
Column 7, line 59: Delete "Table provides" insert --Table 4 provides--
Column 10, line 14: Delete "theological" insert --rheological--
Column 11, line 30: Delete "I-hydrogen" insert --1-hydrogen--
Column 15, line 57: Delete "(51985)" insert -- (1985)--
Column 16, line 25: Delete "Genet. 63:181-187)." insert --Genet. 163:181-187).--
Column 16, line 57: Delete "far example," insert --for example,--

Signed and Sealed this

Fourteenth Day of February, 1995

Attest:

BRUCE LEHMAN

Attesting Officer      Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3797 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Bacillus thuringiensis
        ( B ) STRAIN: japonensis
( C ) INDIVIDUAL ISOLATE: Buibui ( i x ) FEATURE:
( A ) NAME/KEY: CDS
( B ) LOCATION: 187..3636

( x i ) SEQUENCE DESCRIPTION: SEQ ID NO:1:

```
AATTCTAATG ACACAGTAGA ATATTTTTAA AATAAAGATG GAAGGGGGAA TATGAAAAAA      60

ATATAATCAT AAGAGTCATA CAAAAAGATT GTATGTTAAA ACAAAAAAAT CCTGTAGGAA     120

TAGGGGTTTA AAAGCAATCA TTTGAAAAGA TAGTTATATT AAATTGTATG TATAGGGGGA     180

AAAAAG ATG AGT CCA AAT AAT CAA AAT GAG TAT GAA ATT ATA GAT GCT        228
       Met Ser Pro Asn Asn Gln Asn Glu Tyr Glu Ile Ile Asp Ala
        1               5                  10

TTA TCA CCC ACT TCT GTA TCC GAT AAT TCT ATT AGA TAT CCT TTA GCA       276
Leu Ser Pro Thr Ser Val Ser Asp Asn Ser Ile Arg Tyr Pro Leu Ala
 15                  20                  25                  30

AAC GAT CAA ACG AAC ACA TTA CAA AAC ATG AAT TAT AAA GAT TAT CTG       324
Asn Asp Gln Thr Asn Thr Leu Gln Asn Met Asn Tyr Lys Asp Tyr Leu
                 35                  40                  45

AAA ATG ACC GAA TCA ACA AAT GCT GAA TTG TCT CGA AAT CCC GGG ACA       372
Lys Met Thr Glu Ser Thr Asn Ala Glu Leu Ser Arg Asn Pro Gly Thr
             50                  55                  60

TTT ATT AGT GCG CAG GAT GCG GTT GGA ACT GGA ATT GAT ATT GTT AGT       420
Phe Ile Ser Ala Gln Asp Ala Val Gly Thr Gly Ile Asp Ile Val Ser
         65                  70                  75

ACT ATA ATA AGT GGT TTA GGG ATT CCA GTG CTT GGG GAA GTC TTC TCA       468
Thr Ile Ile Ser Gly Leu Gly Ile Pro Val Leu Gly Glu Val Phe Ser
     80                  85                  90

ATT CTG GGT TCA TTA ATT GGC TTA TTG TGG CCG TCA AAT AAT GAA AAT       516
Ile Leu Gly Ser Leu Ile Gly Leu Leu Trp Pro Ser Asn Asn Glu Asn
 95                 100                 105                 110

GTA TGG CAA ATA TTT ATG AAT CGA GTG GAA GAG CTA ATT GAT CAA AAA       564
Val Trp Gln Ile Phe Met Asn Arg Val Glu Glu Leu Ile Asp Gln Lys
                115                 120                 125

ATA TTA GAT TCT GTA AGA TCA AGA GCC ATT GCA GAT TTA GCT AAT TCT       612
Ile Leu Asp Ser Val Arg Ser Arg Ala Ile Ala Asp Leu Ala Asn Ser
            130                 135                 140

AGA ATA GCT GTA GAG TAC TAT CAA AAT GCA CTT GAA GAC TGG AGA AAA       660
Arg Ile Ala Val Glu Tyr Tyr Gln Asn Ala Leu Glu Asp Trp Arg Lys
        145                 150                 155

AAC CCA CAC AGT ACA CGA AGC GCA GCA CTT GTA AAG GAA AGA TTT GGA       708
```

```
        Asn  Pro  His  Ser  Thr  Arg  Ser  Ala  Ala  Leu  Val  Lys  Glu  Arg  Phe  Gly
             160                 165                 170

AAT  GCA  GAA  GCA  ATT  TTA  CGT  ACT  AAC  ATG  GGT  TCA  TTT  TCT  CAA  ACG          756
Asn  Ala  Glu  Ala  Ile  Leu  Arg  Thr  Asn  Met  Gly  Ser  Phe  Ser  Gln  Thr
175                 180                 185                      190

AAT  TAT  GAG  ACT  CCA  CTC  TTA  CCC  ACA  TAT  GCA  CAG  GCC  GCC  TCT  CTG          804
Asn  Tyr  Glu  Thr  Pro  Leu  Leu  Pro  Thr  Tyr  Ala  Gln  Ala  Ala  Ser  Leu
                    195                 200                 205

CAT  TTG  CTT  GTA  ATG  AGG  GAT  GTT  CAA  ATT  TAC  GGG  AAG  GAA  TGG  GGA          852
His  Leu  Leu  Val  Met  Arg  Asp  Val  Gln  Ile  Tyr  Gly  Lys  Glu  Trp  Gly
               210                 215                 220

TAT  CCT  CAA  AAT  GAT  ATT  GAC  CTA  TTT  TAT  AAA  GAA  CAA  GTA  TCT  TAT          900
Tyr  Pro  Gln  Asn  Asp  Ile  Asp  Leu  Phe  Tyr  Lys  Glu  Gln  Val  Ser  Tyr
          225                 230                 235

ACG  GCT  AGA  TAT  TCC  GAT  CAT  TGC  GTC  CAA  TGG  TAC  AAT  GCT  GGT  TTA          948
Thr  Ala  Arg  Tyr  Ser  Asp  His  Cys  Val  Gln  Trp  Tyr  Asn  Ala  Gly  Leu
     240                 245                 250

AAT  AAA  TTA  AGA  GGA  ACG  GGT  GCT  AAG  CAA  TGG  GTG  GAT  TAT  AAT  CGT          996
Asn  Lys  Leu  Arg  Gly  Thr  Gly  Ala  Lys  Gln  Trp  Val  Asp  Tyr  Asn  Arg
255                 260                 265                 270

TTC  CGA  AGA  GAA  ATG  AAT  GTG  ATG  GTA  TTG  GAT  CTA  GTT  GCA  TTA  TTT         1044
Phe  Arg  Arg  Glu  Met  Asn  Val  Met  Val  Leu  Asp  Leu  Val  Ala  Leu  Phe
                    275                 280                 285

CCA  AAC  TAC  GAT  GCG  CGT  ATA  TAT  CCA  CTG  GAA  ACA  AAT  GCA  GAA  CTT         1092
Pro  Asn  Tyr  Asp  Ala  Arg  Ile  Tyr  Pro  Leu  Glu  Thr  Asn  Ala  Glu  Leu
               290                 295                 300

ACA  AGA  GAA  ATT  TTC  ACA  GAT  CCT  GTT  GGA  AGT  TAC  GTA  ACT  GGA  CAA         1140
Thr  Arg  Glu  Ile  Phe  Thr  Asp  Pro  Val  Gly  Ser  Tyr  Val  Thr  Gly  Gln
          305                 310                 315

TCG  AGT  ACC  CTT  ATA  TCT  TGG  TAC  GAT  ATG  ATT  CCA  GCA  GCT  CTT  CCT         1188
Ser  Ser  Thr  Leu  Ile  Ser  Trp  Tyr  Asp  Met  Ile  Pro  Ala  Ala  Leu  Pro
     320                 325                 330

TCA  TTT  TCA  ACG  CTC  GAG  AAC  CTA  CTT  AGA  AAA  CCT  GAT  TTC  TTT  ACT         1236
Ser  Phe  Ser  Thr  Leu  Glu  Asn  Leu  Leu  Arg  Lys  Pro  Asp  Phe  Phe  Thr
335                 340                 345                 350

TTG  CTG  CAA  GAA  ATT  AGA  ATG  TAT  ACA  AGT  TTT  AGA  CAA  AAC  GGT  ACG         1284
Leu  Leu  Gln  Glu  Ile  Arg  Met  Tyr  Thr  Ser  Phe  Arg  Gln  Asn  Gly  Thr
                    355                 360                 365

ATT  GAA  TAT  TAT  AAT  TAT  TGG  GGA  GGA  CAA  AGG  TTA  ACC  CTT  TCT  TAT         1332
Ile  Glu  Tyr  Tyr  Asn  Tyr  Trp  Gly  Gly  Gln  Arg  Leu  Thr  Leu  Ser  Tyr
               370                 375                 380

ATC  TAT  GGT  TCC  TCA  TTC  AAT  AAA  TAT  AGT  GGG  GTT  CTT  GCC  GGT  GCT         1380
Ile  Tyr  Gly  Ser  Ser  Phe  Asn  Lys  Tyr  Ser  Gly  Val  Leu  Ala  Gly  Ala
          385                 390                 395

GAG  GAT  ATT  ATT  CCT  GTG  GGT  CAA  AAT  GAT  ATT  TAC  AGA  GTT  GTA  TGG         1428
Glu  Asp  Ile  Ile  Pro  Val  Gly  Gln  Asn  Asp  Ile  Tyr  Arg  Val  Val  Trp
     400                 405                 410

ACT  TAT  ATA  GGA  AGG  TAC  ACG  AAT  AGT  CTG  CTA  GGA  GTA  AAT  CCA  GTT         1476
Thr  Tyr  Ile  Gly  Arg  Tyr  Thr  Asn  Ser  Leu  Leu  Gly  Val  Asn  Pro  Val
415                 420                 425                 430

ACT  TTT  TAC  TTC  AGT  AAT  AAT  ACA  CAA  AAA  ACT  TAT  TCG  AAG  CCA  AAA         1524
Thr  Phe  Tyr  Phe  Ser  Asn  Asn  Thr  Gln  Lys  Thr  Tyr  Ser  Lys  Pro  Lys
                    435                 440                 445

CAA  TTC  GCG  GGT  GGA  ATA  AAA  ACA  ATT  GAT  TCC  GGC  GAA  GAA  TTA  ACT         1572
Gln  Phe  Ala  Gly  Gly  Ile  Lys  Thr  Ile  Asp  Ser  Gly  Glu  Glu  Leu  Thr
               450                 455                 460

TAC  GAA  AAT  TAT  CAA  TCT  TAT  AGT  CAC  AGG  GTA  AGT  TAC  ATT  ACA  TCT         1620
Tyr  Glu  Asn  Tyr  Gln  Ser  Tyr  Ser  His  Arg  Val  Ser  Tyr  Ile  Thr  Ser
          465                 470                 475

TTT  GAA  ATA  AAA  AGT  ACC  GGT  GGT  ACA  GTA  TTA  GGA  GTA  GTT  CCT  ATA         1668
Phe  Glu  Ile  Lys  Ser  Thr  Gly  Gly  Thr  Val  Leu  Gly  Val  Val  Pro  Ile
     480                 485                 490
```

-continued

| | | | | | | | | | | | | | | | | |
|---|---|---|---|---|---|---|---|---|---|---|---|---|---|---|---|---|
| TTT | GGT | TGG | ACG | CAT | AGT | AGT | GCC | AGT | CGC | AAT | AAC | TTT | ATT | TAC | GCA | 1716 |
| Phe | Gly | Trp | Thr | His | Ser | Ser | Ala | Ser | Arg | Asn | Asn | Phe | Ile | Tyr | Ala | |
| 495 | | | | | 500 | | | | 505 | | | | | | 510 | |
| ACA | AAA | ATC | TCA | CAA | ATC | CCA | ATC | AAT | AAA | GCA | AGT | AGA | ACT | AGC | GGT | 1764 |
| Thr | Lys | Ile | Ser | Gln | Ile | Pro | Ile | Asn | Lys | Ala | Ser | Arg | Thr | Ser | Gly | |
| | | | | 515 | | | | | 520 | | | | | 525 | | |
| GGA | GCG | GTT | TGG | AAT | TTC | CAA | GAA | GGT | CTA | TAT | AAT | GGA | GGA | CCT | GTA | 1812 |
| Gly | Ala | Val | Trp | Asn | Phe | Gln | Glu | Gly | Leu | Tyr | Asn | Gly | Gly | Pro | Val | |
| | | | 530 | | | | | 535 | | | | | 540 | | | |
| ATG | AAA | TTA | TCT | GGG | TCT | GGT | TCC | CAA | GTA | ATA | AAC | TTA | AGG | GTC | GCA | 1860 |
| Met | Lys | Leu | Ser | Gly | Ser | Gly | Ser | Gln | Val | Ile | Asn | Leu | Arg | Val | Ala | |
| | | | 545 | | | | | 550 | | | | | 555 | | | |
| ACA | GAT | GCA | AAG | GGA | GCA | AGT | CAA | AGA | TAT | CGT | ATT | AGA | ATC | AGA | TAT | 1908 |
| Thr | Asp | Ala | Lys | Gly | Ala | Ser | Gln | Arg | Tyr | Arg | Ile | Arg | Ile | Arg | Tyr | |
| | | 560 | | | | | 565 | | | | | 570 | | | | |
| GCC | TCT | GAT | AGA | GCG | GGT | AAA | TTT | ACG | ATA | TCT | TCC | AGA | TCT | CCA | GAG | 1956 |
| Ala | Ser | Asp | Arg | Ala | Gly | Lys | Phe | Thr | Ile | Ser | Ser | Arg | Ser | Pro | Glu | |
| 575 | | | | | 580 | | | | | 585 | | | | | 590 | |
| AAT | CCT | GCA | ACC | TAT | TCA | GCT | TCT | ATT | GCT | TAT | ACA | AAT | ACT | ATG | TCT | 2004 |
| Asn | Pro | Ala | Thr | Tyr | Ser | Ala | Ser | Ile | Ala | Tyr | Thr | Asn | Thr | Met | Ser | |
| | | | | 595 | | | | | 600 | | | | | 605 | | |
| ACA | AAT | GCT | TCT | CTA | ACG | TAT | AGT | ACT | TTT | GCA | TAT | GCA | GAA | TCT | GGC | 2052 |
| Thr | Asn | Ala | Ser | Leu | Thr | Tyr | Ser | Thr | Phe | Ala | Tyr | Ala | Glu | Ser | Gly | |
| | | | | 610 | | | | | 615 | | | | | 620 | | |
| CCT | ATA | AAC | TTA | GGG | ATT | TCG | GGA | AGT | TCA | AGG | ACT | TTT | GAT | ATA | TCT | 2100 |
| Pro | Ile | Asn | Leu | Gly | Ile | Ser | Gly | Ser | Ser | Arg | Thr | Phe | Asp | Ile | Ser | |
| | | 625 | | | | | 630 | | | | | 635 | | | | |
| ATT | ACA | AAA | GAA | GCA | GGT | GCT | GCT | AAC | CTT | TAT | ATT | GAT | AGA | ATT | GAA | 2148 |
| Ile | Thr | Lys | Glu | Ala | Gly | Ala | Ala | Asn | Leu | Tyr | Ile | Asp | Arg | Ile | Glu | |
| | 640 | | | | | 645 | | | | | 650 | | | | | |
| TTT | ATT | CCA | GTT | AAT | ACG | TTA | TTT | GAA | GCA | GAA | GAA | GAC | CTA | GAT | GTG | 2196 |
| Phe | Ile | Pro | Val | Asn | Thr | Leu | Phe | Glu | Ala | Glu | Glu | Asp | Leu | Asp | Val | |
| 655 | | | | | 660 | | | | | 665 | | | | | 670 | |
| GCA | AAG | AAA | GCT | GTG | AAT | GGC | TTG | TTT | ACG | AAT | GAA | AAA | GAT | GCC | TTA | 2244 |
| Ala | Lys | Lys | Ala | Val | Asn | Gly | Leu | Phe | Thr | Asn | Glu | Lys | Asp | Ala | Leu | |
| | | | | 675 | | | | | 680 | | | | | 685 | | |
| CAG | ACA | AGT | GTA | ACG | GAT | TAT | CAA | GTC | AAT | CAA | GCG | GCA | AAC | TTA | ATA | 2292 |
| Gln | Thr | Ser | Val | Thr | Asp | Tyr | Gln | Val | Asn | Gln | Ala | Ala | Asn | Leu | Ile | |
| | | | 690 | | | | | 695 | | | | | 700 | | | |
| GAA | TGC | CTA | TCC | GAT | GAG | TTA | TAC | CCA | AAT | GAA | AAA | CGA | ATG | TTA | TGG | 2340 |
| Glu | Cys | Leu | Ser | Asp | Glu | Leu | Tyr | Pro | Asn | Glu | Lys | Arg | Met | Leu | Trp | |
| | | 705 | | | | | 710 | | | | | 715 | | | | |
| GAT | GCA | GTG | AAA | GAG | GCG | AAA | CGA | CTT | GTT | CAG | GCA | CGT | AAC | TTA | CTC | 2388 |
| Asp | Ala | Val | Lys | Glu | Ala | Lys | Arg | Leu | Val | Gln | Ala | Arg | Asn | Leu | Leu | |
| | 720 | | | | | 725 | | | | | 730 | | | | | |
| CAA | GAT | ACA | GGC | TTT | AAT | AGG | ATT | AAT | GGA | GAA | AAC | GGA | TGG | ACG | GGA | 2436 |
| Gln | Asp | Thr | Gly | Phe | Asn | Arg | Ile | Asn | Gly | Glu | Asn | Gly | Trp | Thr | Gly | |
| 735 | | | | 740 | | | | | 745 | | | | | 750 | | |
| AGT | ACG | GGA | ATC | GAG | GTT | GTG | GAA | GGA | GAT | GTT | CTG | TTT | AAA | GAT | CGT | 2484 |
| Ser | Thr | Gly | Ile | Glu | Val | Val | Glu | Gly | Asp | Val | Leu | Phe | Lys | Asp | Arg | |
| | | | | 755 | | | | | 760 | | | | | 765 | | |
| TCG | CTT | CGT | TTG | ACA | AGT | GCG | AGA | GAG | ATT | GAT | ACA | GAA | ACA | TAT | CCA | 2532 |
| Ser | Leu | Arg | Leu | Thr | Ser | Ala | Arg | Glu | Ile | Asp | Thr | Glu | Thr | Tyr | Pro | |
| | | | 770 | | | | | 775 | | | | | 780 | | | |
| ACG | TAT | CTC | TAT | CAA | CAA | ATA | GAT | GAA | TCG | CTT | TTA | AAA | CCA | TAT | ACA | 2580 |
| Thr | Tyr | Leu | Tyr | Gln | Gln | Ile | Asp | Glu | Ser | Leu | Leu | Lys | Pro | Tyr | Thr | |
| | | 785 | | | | | 790 | | | | | 795 | | | | |
| AGA | TAT | AAA | CTA | AAA | GGT | TTT | ATA | GGA | AGT | AGT | CAA | GAT | TTA | GAG | ATT | 2628 |
| Arg | Tyr | Lys | Leu | Lys | Gly | Phe | Ile | Gly | Ser | Ser | Gln | Asp | Leu | Glu | Ile | |
| | | 800 | | | | | 805 | | | | | 810 | | | | |
| AAA | TTA | ATA | CGT | CAT | CGG | GCA | AAT | CAA | ATC | GTC | AAA | AAT | GTA | CCA | GAT | 2676 |

```
                                    -continued

Lys Leu Ile Arg His Arg Ala Asn Gln Ile Val Lys Asn Val Pro Asp
815                 820                 825                 830

AAT CTC TTG CCA GAT GTA CGC CCT GTC AAT TCT TGT GGT GGA GTC GAT    2724
Asn Leu Leu Pro Asp Val Arg Pro Val Asn Ser Cys Gly Gly Val Asp
                    835                 840                 845

CGC TGC AGT GAA CAA CAG TAT GTA GAC GCG AAT TTA GCA CTC GAA AAC    2772
Arg Cys Ser Glu Gln Gln Tyr Val Asp Ala Asn Leu Ala Leu Glu Asn
                850                 855                 860

AAT GGA GAA AAT GGA AAT ATG TCT TCT GAT TCC CAT GCA TTT TCT TTC    2820
Asn Gly Glu Asn Gly Asn Met Ser Ser Asp Ser His Ala Phe Ser Phe
                865                 870                 875

CAT ATT GAT ACG GGT GAA ATA GAT TTG AAT GAA AAT ACA GGA ATT TGG    2868
His Ile Asp Thr Gly Glu Ile Asp Leu Asn Glu Asn Thr Gly Ile Trp
            880                 885                 890

ATC GTA TTT AAA ATT CCG ACA ACA AAT GGA AAC GCA ACA CTA GGA AAT    2916
Ile Val Phe Lys Ile Pro Thr Thr Asn Gly Asn Ala Thr Leu Gly Asn
895                 900                 905                 910

CTT GAA TTT GTA GAA GAG GGG CCA TTG TCA GGG GAA ACA TTA GAA TGG    2964
Leu Glu Phe Val Glu Glu Gly Pro Leu Ser Gly Glu Thr Leu Glu Trp
                915                 920                 925

GCC CAA CAA CAA GAA CAA CAA TGG CAA GAC AAA ATG GCA AGA AAA CGT    3012
Ala Gln Gln Gln Glu Gln Gln Trp Gln Asp Lys Met Ala Arg Lys Arg
                930                 935                 940

GCA GCA TCA GAA AAA ACA TAT TAT GCA GCA AAG CAA GCC ATT GAT CGT    3060
Ala Ala Ser Glu Lys Thr Tyr Tyr Ala Ala Lys Gln Ala Ile Asp Arg
            945                 950                 955

TTA TTC GCA GAT TAT CAA GAC CAA AAA CTT AAT TCT GGT GTA GAA ATG    3108
Leu Phe Ala Asp Tyr Gln Asp Gln Lys Leu Asn Ser Gly Val Glu Met
960                 965                 970

TCA GAT TTG TTG GCA GCC CAA AAC CTT GTA CAG TCC ATT CCT TAC GTA    3156
Ser Asp Leu Leu Ala Ala Gln Asn Leu Val Gln Ser Ile Pro Tyr Val
975                 980                 985                 990

TAT AAT GAT GCG TTA CCG GAA ATC CCT GGA ATG AAC TAT ACG AGT TTT    3204
Tyr Asn Asp Ala Leu Pro Glu Ile Pro Gly Met Asn Tyr Thr Ser Phe
                995                 1000                1005

ACA GAG TTA ACA AAT AGA CTC CAA CAA GCA TGG AAT TTG TAT GAT CTT    3252
Thr Glu Leu Thr Asn Arg Leu Gln Gln Ala Trp Asn Leu Tyr Asp Leu
            1010                1015                1020

CAA AAC GCT ATA CCA AAT GGA GAT TTT CGA AAT GGA TTA AGT AAT TGG    3300
Gln Asn Ala Ile Pro Asn Gly Asp Phe Arg Asn Gly Leu Ser Asn Trp
            1025                1030                1035

AAT GCA ACA TCA GAT GTA AAT GTG CAA CAA CTA AGC GAT ACA TCT GTC    3348
Asn Ala Thr Ser Asp Val Asn Val Gln Gln Leu Ser Asp Thr Ser Val
        1040                1045                1050

CTT GTC ATT CCA AAC TGG AAT TCT CAA GTG TCA CAA CAA TTT ACA GTT    3396
Leu Val Ile Pro Asn Trp Asn Ser Gln Val Ser Gln Gln Phe Thr Val
1055                1060                1065                1070

CAA CCG AAT TAT AGA TAT GTG TTA CGT GTC ACA GCG AGA AAA GAG GGA    3444
Gln Pro Asn Tyr Arg Tyr Val Leu Arg Val Thr Ala Arg Lys Glu Gly
                1075                1080                1085

GTA GGA GAC GGA TAT GTG ATC ATC CGT GAT GGT GCA AAT CAG ACA GAA    3492
Val Gly Asp Gly Tyr Val Ile Ile Arg Asp Gly Ala Asn Gln Thr Glu
            1090                1095                1100

ACA CTC ACA TTT AAT ATA TGT GAT GAT GAT ACA GGT GTT TTA TCT ACT    3540
Thr Leu Thr Phe Asn Ile Cys Asp Asp Asp Thr Gly Val Leu Ser Thr
        1105                1110                1115

GAT CAA ACT AGC TAT ATC ACA AAA ACA GTG GAA TTC ACT CCA TCT ACA    3588
Asp Gln Thr Ser Tyr Ile Thr Lys Thr Val Glu Phe Thr Pro Ser Thr
    1120                1125                1130

GAG CAA GTT TGG ATT GAC ATG AGT GAG ACC GAA GTG TAT TCA ACA TAGAAAGT 3643
Glu Gln Val Trp Ile Asp Met Ser Glu Thr Glu Val Tyr Ser Thr
1135                1140                1145            1149
```

| | | | | | | | | |
|---|---|---|---|---|---|---|---|---|
| AGAACTCGTG | TTAGAAGAAG | AGTAATCATA | GTTTCCCTCC | AGATAGAAGG | TTGATCTGGA | | | 3703 |
| GGTTTTCTTA | TAGAGAGAGT | ACTATGAATC | AAATGTTTGA | TGAATGCGTT | GCGAGCGGTT | | | 3763 |
| TATCTCAAAT | ATCAACGGTA | CAAGGTTTAT | AAAT | | | | | 3797 |

( 2 ) INFORMATION FOR SEQ ID NO:2:

( i ) SEQUENCE CHARACTERISTICS:
        ( A ) LENGTH: 1149 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ser  Pro  Asn  Asn  Gln  Asn  Glu  Tyr  Glu  Ile  Ile  Asp  Ala  Leu  Ser
 1              5                        10                       15

Pro  Thr  Ser  Val  Ser  Asp  Asn  Ser  Ile  Arg  Tyr  Pro  Leu  Ala  Asn  Asp
              20                       25                       30

Gln  Thr  Asn  Thr  Leu  Gln  Asn  Met  Asn  Tyr  Lys  Asp  Tyr  Leu  Lys  Met
         35                        40                       45

Thr  Glu  Ser  Thr  Asn  Ala  Glu  Leu  Ser  Arg  Asn  Pro  Gly  Thr  Phe  Ile
     50                        55                       60

Ser  Ala  Gln  Asp  Ala  Val  Gly  Thr  Gly  Ile  Asp  Ile  Val  Ser  Thr  Ile
 65                       70                       75                       80

Ile  Ser  Gly  Leu  Gly  Ile  Pro  Val  Leu  Gly  Glu  Val  Phe  Ser  Ile  Leu
                   85                       90                       95

Gly  Ser  Leu  Ile  Gly  Leu  Leu  Trp  Pro  Ser  Asn  Asn  Glu  Asn  Val  Trp
                   100                      105                      110

Gln  Ile  Phe  Met  Asn  Arg  Val  Glu  Glu  Leu  Ile  Asp  Gln  Lys  Ile  Leu
              115                      120                      125

Asp  Ser  Val  Arg  Ser  Arg  Ala  Ile  Ala  Asp  Leu  Ala  Asn  Ser  Arg  Ile
         130                      135                      140

Ala  Val  Glu  Tyr  Tyr  Gln  Asn  Ala  Leu  Glu  Asp  Trp  Arg  Lys  Asn  Pro
145                      150                      155                      160

His  Ser  Thr  Arg  Ser  Ala  Ala  Leu  Val  Lys  Glu  Arg  Phe  Gly  Asn  Ala
                   165                      170                      175

Glu  Ala  Ile  Leu  Arg  Thr  Asn  Met  Gly  Ser  Phe  Ser  Gln  Thr  Asn  Tyr
              180                      185                      190

Glu  Thr  Pro  Leu  Leu  Pro  Thr  Tyr  Ala  Gln  Ala  Ala  Ser  Leu  His  Leu
         195                      200                      205

Leu  Val  Met  Arg  Asp  Val  Gln  Ile  Tyr  Gly  Lys  Glu  Trp  Gly  Tyr  Pro
     210                      215                      220

Gln  Asn  Asp  Ile  Asp  Leu  Phe  Tyr  Lys  Glu  Gln  Val  Ser  Tyr  Thr  Ala
225                      230                      235                      240

Arg  Tyr  Ser  Asp  His  Cys  Val  Gln  Trp  Tyr  Asn  Ala  Gly  Leu  Asn  Lys
                   245                      250                      255

Leu  Arg  Gly  Thr  Gly  Ala  Lys  Gln  Trp  Val  Asp  Tyr  Asn  Arg  Phe  Arg
              260                      265                      270

Arg  Glu  Met  Asn  Val  Met  Val  Leu  Asp  Leu  Val  Ala  Leu  Phe  Pro  Asn
         275                      280                      285

Tyr  Asp  Ala  Arg  Ile  Tyr  Pro  Leu  Glu  Thr  Asn  Ala  Glu  Leu  Thr  Arg
     290                      295                      300

Glu  Ile  Phe  Thr  Asp  Pro  Val  Gly  Ser  Tyr  Val  Thr  Gly  Gln  Ser  Ser
305                      310                      315                      320

Thr  Leu  Ile  Ser  Trp  Tyr  Asp  Met  Ile  Pro  Ala  Ala  Leu  Pro  Ser  Phe
                   325                      330                      335
```

-continued

| | | | | | | | | | | | | | | |
|---|---|---|---|---|---|---|---|---|---|---|---|---|---|---|
| Ser | Thr | Leu | Glu<br>340 | Asn | Leu | Leu | Arg | Lys<br>345 | Pro | Asp | Phe | Phe | Thr<br>350 | Leu | Leu |
| Gln | Glu | Ile | Arg<br>355 | Met | Tyr | Thr | Ser | Phe<br>360 | Arg | Gln | Asn | Gly | Thr<br>365 | Ile | Glu |
| Tyr | Tyr | Asn<br>370 | Tyr | Trp | Gly | Gly<br>375 | Gln | Arg | Leu | Thr | Leu<br>380 | Ser | Tyr | Ile | Tyr |
| Gly<br>385 | Ser | Ser | Phe | Asn | Lys<br>390 | Tyr | Ser | Gly | Val | Leu<br>395 | Ala | Gly | Ala | Glu | Asp<br>400 |
| Ile | Ile | Pro | Val | Gly<br>405 | Gln | Asn | Asp | Ile | Tyr<br>410 | Arg | Val | Val | Trp | Thr<br>415 | Tyr |
| Ile | Gly | Arg | Tyr<br>420 | Thr | Asn | Ser | Leu | Leu<br>425 | Gly | Val | Asn | Pro | Val<br>430 | Thr | Phe |
| Tyr | Phe | Ser<br>435 | Asn | Asn | Thr | Gln | Lys<br>440 | Thr | Tyr | Ser | Lys | Pro<br>445 | Lys | Gln | Phe |
| Ala | Gly<br>450 | Gly | Ile | Lys | Thr | Ile<br>455 | Asp | Ser | Gly | Glu<br>460 | Glu | Leu | Thr | Tyr | Glu |
| Asn<br>465 | Tyr | Gln | Ser | Tyr | Ser<br>470 | His | Arg | Val | Ser | Tyr<br>475 | Ile | Thr | Ser | Phe | Glu<br>480 |
| Ile | Lys | Ser | Thr | Gly<br>485 | Gly | Thr | Val | Leu | Gly<br>490 | Val | Val | Pro | Ile | Phe<br>495 | Gly |
| Trp | Thr | His | Ser<br>500 | Ser | Ala | Ser | Arg | Asn<br>505 | Asn | Phe | Ile | Tyr | Ala<br>510 | Thr | Lys |
| Ile | Ser | Gln<br>515 | Ile | Pro | Ile | Asn | Lys<br>520 | Ala | Ser | Arg | Thr | Ser<br>525 | Gly | Gly | Ala |
| Val | Trp<br>530 | Asn | Phe | Gln | Glu | Gly<br>535 | Leu | Tyr | Asn | Gly | Gly<br>540 | Pro | Val | Met | Lys |
| Leu<br>545 | Ser | Gly | Ser | Gly | Ser<br>550 | Gln | Val | Ile | Asn | Leu<br>555 | Arg | Val | Ala | Thr | Asp<br>560 |
| Ala | Lys | Gly | Ala | Ser<br>565 | Gln | Arg | Tyr | Arg | Ile<br>570 | Arg | Ile | Arg | Tyr | Ala<br>575 | Ser |
| Asp | Arg | Ala | Gly<br>580 | Lys | Phe | Thr | Ile | Ser<br>585 | Ser | Arg | Ser | Pro | Glu<br>590 | Asn | Pro |
| Ala | Thr | Tyr<br>595 | Ser | Ala | Ser | Ile | Ala<br>600 | Tyr | Thr | Asn | Thr | Met<br>605 | Ser | Thr | Asn |
| Ala | Ser<br>610 | Leu | Thr | Tyr | Ser | Thr<br>615 | Phe | Ala | Tyr | Ala | Glu<br>620 | Ser | Gly | Pro | Ile |
| Asn<br>625 | Leu | Gly | Ile | Ser | Gly<br>630 | Ser | Ser | Arg | Thr | Phe<br>635 | Asp | Ile | Ser | Ile | Thr<br>640 |
| Lys | Glu | Ala | Gly | Ala<br>645 | Ala | Asn | Leu | Tyr | Ile<br>650 | Asp | Arg | Ile | Glu | Phe<br>655 | Ile |
| Pro | Val | Asn | Thr<br>660 | Leu | Phe | Glu | Ala | Glu<br>665 | Glu | Asp | Leu | Asp | Val<br>670 | Ala | Lys |
| Lys | Ala | Val<br>675 | Asn | Gly | Leu | Phe | Thr<br>680 | Asn | Glu | Lys | Asp | Ala<br>685 | Leu | Gln | Thr |
| Ser | Val<br>690 | Thr | Asp | Tyr | Gln | Val<br>695 | Asn | Gln | Ala | Ala | Asn<br>700 | Leu | Ile | Glu | Cys |
| Leu<br>705 | Ser | Asp | Glu | Leu | Tyr<br>710 | Pro | Asn | Glu | Lys | Arg<br>715 | Met | Leu | Trp | Asp | Ala<br>720 |
| Val | Lys | Glu | Ala | Lys<br>725 | Arg | Leu | Val | Gln | Ala<br>730 | Arg | Asn | Leu | Leu | Gln<br>735 | Asp |
| Thr | Gly | Phe | Asn<br>740 | Arg | Ile | Asn | Gly | Glu<br>745 | Asn | Gly | Trp | Thr | Gly<br>750 | Ser | Thr |
| Gly | Ile | Glu<br>755 | Val | Val | Glu | Gly | Asp<br>760 | Val | Leu | Phe | Lys | Asp<br>765 | Arg | Ser | Leu |
| Arg | Leu | Thr | Ser | Ala | Arg | Glu | Ile | Asp | Thr | Glu | Thr | Tyr | Pro | Thr | Tyr |

```
                770                        775                          780
Leu  Tyr  Gln  Gln  Ile  Asp  Glu  Ser  Leu  Leu  Lys  Pro  Tyr  Thr  Arg  Tyr
785                      790                      795                          800

Lys  Leu  Lys  Gly  Phe  Ile  Gly  Ser  Ser  Gln  Asp  Leu  Glu  Ile  Lys  Leu
                    805                      810                     815

Ile  Arg  His  Arg  Ala  Asn  Gln  Ile  Val  Lys  Asn  Val  Pro  Asp  Asn  Leu
               820                      825                     830

Leu  Pro  Asp  Val  Arg  Pro  Val  Asn  Ser  Cys  Gly  Gly  Val  Asp  Arg  Cys
          835                      840                     845

Ser  Glu  Gln  Gln  Tyr  Val  Asp  Ala  Asn  Leu  Ala  Leu  Glu  Asn  Asn  Gly
     850                      855                     860

Glu  Asn  Gly  Asn  Met  Ser  Ser  Asp  Ser  His  Ala  Phe  Ser  Phe  His  Ile
865                      870                     875                          880

Asp  Thr  Gly  Glu  Ile  Asp  Leu  Asn  Glu  Asn  Thr  Gly  Ile  Trp  Ile  Val
                    885                      890                     895

Phe  Lys  Ile  Pro  Thr  Thr  Asn  Gly  Asn  Ala  Thr  Leu  Gly  Asn  Leu  Glu
               900                      905                     910

Phe  Val  Glu  Glu  Gly  Pro  Leu  Ser  Gly  Glu  Thr  Leu  Glu  Trp  Ala  Gln
          915                      920                     925

Gln  Gln  Glu  Gln  Gln  Trp  Gln  Asp  Lys  Met  Ala  Arg  Lys  Arg  Ala  Ala
     930                      935                     940

Ser  Glu  Lys  Thr  Tyr  Tyr  Ala  Ala  Lys  Gln  Ala  Ile  Asp  Arg  Leu  Phe
945                      950                     955                          960

Ala  Asp  Tyr  Gln  Asp  Gln  Lys  Leu  Asn  Ser  Gly  Val  Glu  Met  Ser  Asp
                    965                      970                     975

Leu  Leu  Ala  Ala  Gln  Asn  Leu  Val  Gln  Ser  Ile  Pro  Tyr  Val  Tyr  Asn
               980                      985                     990

Asp  Ala  Leu  Pro  Glu  Ile  Pro  Gly  Met  Asn  Tyr  Thr  Ser  Phe  Thr  Glu
          995                     1000                    1005

Leu  Thr  Asn  Arg  Leu  Gln  Gln  Ala  Trp  Asn  Leu  Tyr  Asp  Leu  Gln  Asn
     1010                     1015                    1020

Ala  Ile  Pro  Asn  Gly  Asp  Phe  Arg  Asn  Gly  Leu  Ser  Asn  Trp  Asn  Ala
1025                     1030                    1035                         1040

Thr  Ser  Asp  Val  Asn  Val  Gln  Gln  Leu  Ser  Asp  Thr  Ser  Val  Leu  Val
                    1045                     1050                    1055

Ile  Pro  Asn  Trp  Asn  Ser  Gln  Val  Ser  Gln  Gln  Phe  Thr  Val  Gln  Pro
               1060                     1065                    1070

Asn  Tyr  Arg  Tyr  Val  Leu  Arg  Val  Thr  Ala  Arg  Lys  Glu  Gly  Val  Gly
          1075                     1080                    1085

Asp  Gly  Tyr  Val  Ile  Ile  Arg  Asp  Gly  Ala  Asn  Gln  Thr  Glu  Thr  Leu
     1090                     1095                    1100

Thr  Phe  Asn  Ile  Cys  Asp  Asp  Thr  Gly  Val  Leu  Ser  Thr  Asp  Gln
1105                     1110                    1115                         1120

Thr  Ser  Tyr  Ile  Thr  Lys  Thr  Val  Glu  Phe  Thr  Pro  Ser  Thr  Glu  Gln
                    1125                     1130                    1135

Val  Trp  Ile  Asp  Met  Ser  Glu  Thr  Glu  Val  Tyr  Ser  Thr
               1140                     1145
```